US012797091B2

(12) United States Patent
Yan et al.

(10) Patent No.: US 12,797,091 B2
(45) Date of Patent: Nov. 17, 2026

(54) SHOCK WAVE CATHETER, ELECTRODE CONNECTION STRUCTURE AND CONTROL SYSTEM

(71) Applicant: SHANGHAI JMY MEDICAL CO., LTD, Shanghai (CN)

(72) Inventors: Yonggang Yan, Shanghai (CN); Lifu Li, Shanghai (CN); Tianji Yan, Shanghai (CN); Zonghu Yang, Shanghai (CN)

(73) Assignee: SHANGHAI JMY MEDICAL CO., LTD, Shanghai (CN)

( * ) Notice: Subject to any disclaimer, the term of this patent is extended or adjusted under 35 U.S.C. 154(b) by 139 days.

(21) Appl. No.: 18/862,053

(22) PCT Filed: Apr. 17, 2024

(86) PCT No.: PCT/CN2024/088233

§ 371 (c)(1),
(2) Date: Oct. 31, 2024

(87) PCT Pub. No.: WO2024/250844

PCT Pub. Date: Dec. 12, 2024

(65) Prior Publication Data

US 2026/0102173 A1 Apr. 16, 2026

(30) Foreign Application Priority Data

Jun. 6, 2023 (CN) ........................ 202310659929.4

(51) Int. Cl.
*A61B 17/22* (2006.01)
*G16H 40/63* (2018.01)
(Continued)

(52) U.S. Cl.
CPC .. *A61B 17/22022* (2013.01); *A61B 17/22029* (2013.01); *G16H 40/63* (2018.01);
(Continued)

(58) Field of Classification Search
CPC ........ A61B 17/22022; A61B 17/22029; A61B 17/225; A61B 17/2251
See application file for complete search history.

(56) References Cited

U.S. PATENT DOCUMENTS

2017/0265942 A1 9/2017 Grace et al.
2021/0275247 A1 9/2021 Schultheis et al.
(Continued)

FOREIGN PATENT DOCUMENTS

CN 104582621 A 4/2015
CN 112842460 A 5/2021
(Continued)

*Primary Examiner* — Martin T Ton

(74) *Attorney, Agent, or Firm* — MUNCY, GEISSLER, OLDS & LOWE, P.C.

(57) ABSTRACT

A shock wave catheter includes a catheter body including inner and outer tubes and a balloon connected to a distal end of the catheter body and provided thereon with a pressure sensor for monitoring a pressure profile within the balloon. The catheter body defines a fluid passage for introducing or discharging a medium into and from the balloon. A shock wave source is disposed on the inner tube to deliver pulses with energy according to the pressure profile. Through monitoring the pressure profile within the balloon during its operation using the pressure sensor disposed on the balloon, in the event of a rupture of the balloon due to some reason, the pressure sensor can quickly identify the abnormality, thereby effectively avoiding possible damage to a human body caused by otherwise continued electric discharge to the human body in the presence of the rupture in the balloon.

15 Claims, 4 Drawing Sheets

(51) Int. Cl.
*A61B 17/00* (2006.01)
*A61B 90/00* (2016.01)

(52) U.S. Cl.
CPC ............... *A61B 2017/00022* (2013.01); *A61B 2017/22025* (2013.01); *A61B 2017/22051* (2013.01); *A61B 2090/064* (2016.02)

(56) References Cited

U.S. PATENT DOCUMENTS

| | | | | |
|---|---|---|---|---|
| 2023/0123003 | A1 | 4/2023 | Vo | |
| 2023/0248376 | A1* | 8/2023 | Anderson ........... | A61M 25/104 |
| 2024/0173044 | A1* | 5/2024 | Chen ................ | A61B 17/22022 |

FOREIGN PATENT DOCUMENTS

| | | | |
|---|---|---|---|
| CN | 112869825 | A | 6/2021 |
| CN | 113648048 | A | 11/2021 |
| CN | 113951972 | A | 1/2022 |
| CN | 215458401 | U * | 1/2022 |
| CN | 115066214 | A | 9/2022 |
| CN | 115137446 | A | 10/2022 |
| CN | 115154858 | A | 10/2022 |
| CN | 115192122 | A | 10/2022 |
| CN | 115317071 | A | 11/2022 |
| CN | 218960855 | U | 5/2023 |
| CN | 116392203 | A | 7/2023 |
| WO | WO2021162855 | A1 | 8/2021 |
| WO | WO2023039309 | A1 | 3/2023 |

* cited by examiner

SHOCK WAVE CATHETER, ELECTRODE CONNECTION STRUCTURE AND CONTROL SYSTEM

TECHNICAL FIELD

The present invention relates to the field of medical devices, and particularly to a shock wave catheter, an electrode connection structure and a control system.

BACKGROUND

Vascular calcification refers to the pathological deposition of calcific masses within a blood vessel wall, which hardens the blood vessel wall, reduces its compliance and tends to induce myocardial ischemia, left ventricular hypertrophy, heart failure, thrombosis, plaque disruption and other conditions associated with high rates of mortality and disability. A calcified blood vessel can be treated by dilation with a minimally invasive device such as a balloon or stent to increase blood flow. However, since the calcified portion is hard and lacks compliance, advancing the device through the portion is difficult and associated with an increased risk of causing percutaneous coronary intervention (PCI)-related complications, such as failure of the interventional device to reach the lesion site, premature stent detachment, guidewire breakage and longitudinal stent compression, which may ultimately affect the therapeutic outcomes. A recent new technique developed abroad involves inserting a catheter with a distal balloon into a calcified blood vessel and expanding the balloon against the wall of the blood vessel at the calcified target lesion so that electrodes in the balloon connected to a high-voltage generator can serve as electro-hydraulic wave sources, which, when excited, delivers high-voltage pulses for producing shock waves through cavitation. The resulting shock waves propagate through a liquid medium to a wall of the balloon, where they strike and crush calcific masses in the vessel wall, remodeling the blood vessel to make it elastic and compliant again without causing damage to the inner wall or intima of the blood vessel.

However, the balloon used in this conventional technique is non-compliant or semi-compliant, and the electrodes therein create radial shock waves. Such a balloon would not be able to pass through a heavily calcified lesion to deliver radial shock waves thereto, making the technique difficult to use in the treatment of such lesions. Moreover, for asymmetric lesions with complex anatomy, the non-compliant balloon cannot be expanded sufficiently against a blood vessel wall, making the energy of shock waves unable to be delivered to the surface of calcific masses. Consequently, unsatisfactory therapeutic outcomes would be expected.

Notably, Pat. App. Pub. No. CN115192122A, previously filed by the applicant, discloses a shock wave balloon catheter device, which, when advanced to a heavily calcified lesion that it cannot be passed through, is positioned with the aid of X-ray radiography so that a distal end of its balloon is located at the lesion. A conductive medium is then injected to expand the balloon so that its distal end presses against the calcified lesion and its side wall against the blood vessel wall. At this time, a high-voltage generator is activated to energize a first shock wave source to allow it to deliver axial shock waves toward the distal balloon end to soften the lesion. After that, part of the conductive medium is drawn out to contract the balloon so that it can be passed through the lesion. The balloon is then advanced to a location where its side wall is aligned with the calcified lesion, and the conductive medium is again injected to expand the balloon. Subsequently, the high-voltage generator is activated to energize a second shock wave source, which then delivers radial shock waves toward the balloon's side wall to crush the calcified lesion. At the same time, the conductive medium continues being injected to increasingly expand the balloon to flatten and compact the crushed calcific masses onto the inner wall of the blood vessel, thus restoring blood flow. However, this solution has been found to suffer from a number of drawbacks during use in practical applications. 1. During operation of the catheter device, it is impossible to monitor energy that is delivered to a human body. This is problematic because sometimes calcific masses within a lesion site may be so hard or sharp as to possibly rupture the balloon. When this happens, continued electric discharge may cause damage to the human body. 2. During practical use, since the balloon from which shock waves are delivered is inserted within a human body, it is impossible to check whether the catheter is operating appropriately from the outside. 3. When used to treat a very severely calcified lesion, the required energy may exceed predetermined maximum energy that the shock wave source can provide. 4. The shock wave catheter includes a number of electrodes, which are usually grouped into sets connected in series, as with those in other known shock wave catheters (e.g., the low-profile electrodes employed in the shock wave catheter for use in angioplasty, disclosed in Pat. App. Pub. No. CN104582621B). However, the use of multiple such series-connected sets of electrodes requires frequent circuit switching during operation of the shock wave catheter, which will shorten the service life of the switch used and hence of the high-voltage generator.

SUMMARY

In order to solve the above-described problems, the present invention provides a shock wave catheter including a balloon and a catheter body. The balloon is connected to a distal end of the catheter body and provided thereon with a number of pressure sensors for detecting pressures at different locations on a surface of the balloon, which represent a pressure profile.

The catheter body includes an inner tube and an outer tube. The outer tube is disposed over the inner tube. The catheter body defines a fluid passage adapted for input and output of a medium into and from the balloon.

The inner tube is provided thereon with shock wave source for delivering pulses.

The shock wave source delivers pulses with energy according to the pressure profile.

Preferably, a plurality of pressure sensors may be provide on a wall of the balloon at intervals to monitor the pressure profile on the surface of the balloon, at least one of which is aligned with a set of electrodes in the shock wave source.

Preferably, the shock wave source may include at least a first set of electrodes and a second set of electrodes, which each include a first electrode and a second electrode, wherein the first electrode in the first set of electrodes and the second electrode in the second set of electrodes are connected to a control system, wherein the second electrode in the first set of electrodes is connected to the first electrode in the second set of electrodes, and wherein at least one of the pressure sensors is provided on the balloon at a location aligned with the midpoint of a gap between the first set of electrodes and the second set of electrodes.

Preferably, the shock wave source may include at least a first set of electrodes, a second set of electrodes and a third set of electrode, wherein the first set of electrodes is adjacent to the second set of electrodes, wherein the first set of electrodes and the second set of electrodes each include a first electrode and a second electrode, wherein the second electrode in the first set of electrodes is electrically connected to the second electrode in the second set of electrodes, wherein one of the first electrode in the first set of electrodes and the first electrode in the second set of electrodes is electrically connected to a first electrode in the third set of electrodes and to the control system, wherein the other of the first electrode in the first set of electrodes and the first electrode in the second set of electrodes and a second electrode in the third set of electrodes are connected to the control system.

Additionally, the pressure sensors may include a first pressure sensor and a second pressure sensor, wherein the first pressure sensor is provided on the balloon at a location aligned with the midpoint of a gap between the first set of electrodes and the second set of electrodes, and the second pressure sensor is provided on the balloon at a location aligned with the third set of electrodes.

Preferably, each set of electrodes in the shock wave source may include a first electrode, a second electrode and an insulator layer, wherein the first electrode is embedded in the second electrode, wherein the insulator layer is situated between the second electrode and the first electrode, and wherein the second electrode and the insulator layer each define a discharge aperture.

Preferably, each set of electrodes in the shock wave source may include a first electrode, a second electrode and an insulator layer, wherein the first electrode and the second electrode are arranged side by side, wherein the insulator layer is situated between the first electrode and the inner tube and between the second electrode and the inner tube, and wherein the first electrode and the second electrode define a discharge aperture therebetween.

Preferably, each set of electrodes in the shock wave source may include a first electrode, a second electrode and an insulator layer, wherein the first electrode and the second electrode are both embedded in the insulator layer on opposite sides of the inner tube, wherein an outer electrode is disposed over the insulator layer, and wherein the insulator layer and the outer electrode each define a discharge aperture.

An electrode connection structure is also provided, which includes a shock wave source and a high-voltage generator. The shock wave source includes at least one set of electrodes, which is/are wired in parallel, in series or in both series and parallel and connected to the high-voltage generator. Each set of electrodes includes at least first electrode, a second electrode and a discharge aperture.

Preferably, the shock wave source may be composed of one set of electrodes including a first electrode and a second electrode, which are separately wired to the high-voltage generator.

Preferably, the shock wave source may be composed of two sets of electrodes, namely a first set of electrodes and a second set of electrodes, each of which includes a first electrode and a second electrode.

In a first connection method, the second electrode in the first set of electrodes is wired to the second electrode in the second set of electrodes, and the first electrode in the first set of electrodes and the first electrode in the second set of electrodes are wired to the high-voltage generator.

In a second connection method, the first electrode in the first set of electrodes is wired to the first electrode in the second set of electrodes, and the second electrode in the first set of electrodes is wired to the second electrode in the second set of electrodes. Moreover, both pairs are wired to the high-voltage generator.

Preferably, the shock wave source may be composed of three sets of electrodes, namely, a first set of electrodes, a second set of electrodes and a third set of electrodes, each of which includes a first electrode and a second electrode.

In a first connection method, the first electrode in the first set of electrodes, the first electrode in the second set of electrodes and the first electrode in the third set of electrodes are connected in parallel and then to the high-voltage generator. Moreover, the second electrode in the first set of electrodes, the second electrode in the second set of electrodes and a third electrode in the third set of electrodes are connected in parallel and then to the high-voltage generator.

In a second connection method, the first electrode in the first set of electrodes and the first electrode in the second set of electrodes are wired in parallel and then to the high-voltage generator, and the first electrode in the third set of electrodes is wired to the high-voltage generator. Moreover, the second electrode in the first set of electrodes, the second electrode in the second set of electrodes and the second electrode in the third set of electrodes are connected to the high-voltage generator.

In a third connection method, the first electrode in the first set of electrodes is wired to the high-voltage generator, and the second electrode in the first set of electrodes is wired in series with the second electrode in the second set of electrodes. Moreover, the first electrode in the third set of electrodes is wired to the high-voltage generator, and the first electrode in the second set of electrodes and the second electrode in the third set of electrodes are connected to the high-voltage generator.

A control system is also provided, which includes:

- a data reception module for receiving pressure values from pressure sensors operating at different locations;
- a monitoring and analysis module for receiving the pressure values, analyzing a pressure profile that they represent and outputting a result of analysis; and
- an energy control module for generating a control signal based on the result of analysis, which is used to adjust energy with which pulses are delivered from a shock wave source.

Preferably, when a change indicated by the pressure values that the monitoring and analysis module receives exceeds a first predetermined threshold, the energy control module may generate a power-off signal for deactivating the shock wave source and ceasing its output of pulses.

Preferably, when the pressure values that the monitoring and analysis module receives are higher than a first predetermined pressure value, the energy control module may control the shock wave source to deliver pulses with less energy.

Preferably, when the pressure values that the monitoring and analysis module receives are lower than a second predetermined pressure value, the energy control module may control the shock wave source to deliver pulses with more energy.

Preferably, when the pressure values that the monitoring and analysis module receives are lower than a third predetermined pressure value that is in turn lower than the second predetermined pressure value, the energy control module may generate an error report signal and stop output of the pulses.

Preferably, when the change indicated by the pressure values that the monitoring and analysis module receives is less than a second predetermined threshold, the energy control module may control the shock wave source to deliver pulses with more energy.

The present invention has the following benefits and advantages:

1. The pressure sensors arranged on the balloon can monitor a pressure profile within the balloon during its operation. In the event of a rupture in the balloon due to some reason, the pressure sensors can quickly locate the abnormality, thereby effectively avoiding possible damage to a human body caused by otherwise continued electric discharge to the human body in the presence of the rupture in the balloon.
2. After a period of continued operation, energy of shock waves delivered to the balloon will more or less attenuate. According to the present invention, energy of shock waves arriving at the balloon surface can be monitored, and when it attenuates to a given threshold, the control system will deliver shock waves with more energy, ensuring their effectiveness.
3. In operation, the pressure sensors always monitor a pressure profile across the balloon surface and hence operation of the shock wave source. When the balloon or shock wave source experiences an abnormal condition, the control system can notify an operator of the abnormality in a timely way, avoiding possible damage to a human body from affecting safety. When an electrode in the shock wave generator becomes abnormal (unable to deliver pulses), a corresponding pressure sensor may raise a signal indicative of the abnormality to the control system in a timely manner. This can provide guidance to the operator and avoid the abnormality from affecting effectiveness of the treatment.
4. As the balloon is inserted within a human body during a surgical procedure, it is in no way to determine whether the catheter is operating properly or not from the outside. The present invention overcomes this by employing the pressure sensors which can be used to determine whether any electrode is operating abnormally or not (when a pressure value from a pressure sensor is lower than a predetermined value, it can be determined that the corresponding electrode fails).
5. The sets of electrodes may be connected according to any of multiple methods (in series, in parallel or in both series and parallel). A parallel connection allows simultaneous electric discharge from multiple electrodes, effectively avoiding frequent circuit switching, which may shorten the service life of the switch used and hence of the high-voltage generator. Moreover, a parallel connection allows the shock wave source to deliver shock waves with less energy, enabling safer use.

LIST OF REFERENCE NUMERALS

01 balloon; 02, pressure sensor; 04, shock wave source; 05, inner tube; 06, outer tube; 07, catheter body; 042, first set of electrodes; 043, second set of electrodes; 044, third set of electrodes; 0411, first electrode; 0412, second electrode; 0413, insulator layer; 0414, discharge aperture; 0415, outer electrode; 10, control system; 11, data reception module; 12, monitoring and analysis module; 13, energy control module.

DETAILED DESCRIPTION

The present invention will be described below in greater detail with the accompanying drawings which illustrate specific embodiments thereof. The description of the present invention has been presented for purposes of illustration and description, but is not intended to be exhaustive or limited to the invention in the form disclosed. Many modifications and variations will be apparent to those of ordinary skill in the art. The embodiments are chosen and described in order to best explain the principles of the invention and the practical application, and to enable others of ordinary skill in the art to understand the invention for various embodiments with various modifications, as are suited to the particular use contemplated.

Figure 1:
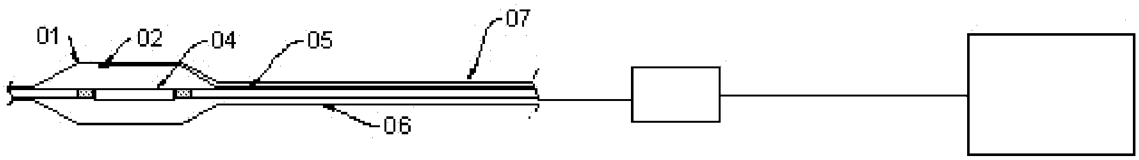
FIG. 1 depicts a schematic structural view of a shock wave catheter according to an embodiment of the present application.
Figure 2:
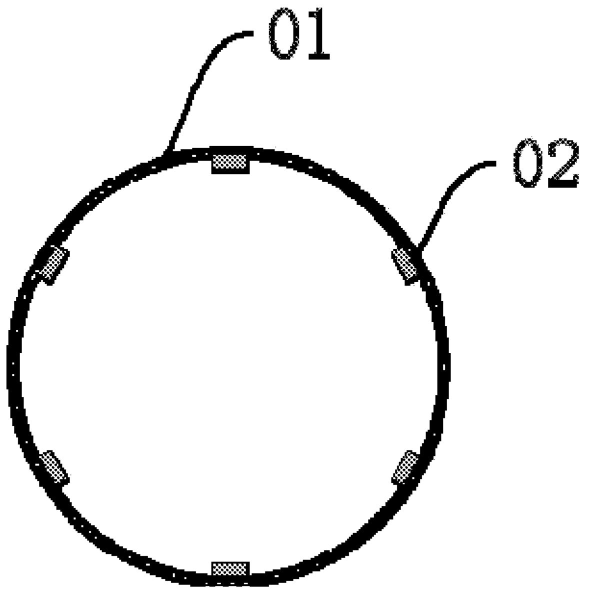
FIG. 2 depicts a schematic cross-sectional view of a balloon in a shock wave catheter according to an embodiment of the present application.

As shown in FIGS. 1 to 2, an embodiment of the present invention provides a shock wave catheter including a balloon 01 and a catheter body 07. The balloon 01 is connected to a distal end of the catheter body 07, and a number of pressure sensors 02 are provided on the balloon 01, the pressure sensors 02 are electrically connected to a control system 10. The catheter body 07 includes an outer tube 06 and an inner tube 05. The catheter body 07 defines a fluid passage, through which a liquid can be introduced into or discharged from the balloon 01 to expand or contract the balloon 01 within a blood vessel. The fluid passage may be in any suitable form, as required. In this embodiment, a space between the outer tube 06 and the inner tube 05 may act as the fluid passage, and the liquid introduced or discharged through the fluid passage may be physiological saline, a contrast medium or a mixture thereof. An end of the catheter body 07 away from the balloon 01 is sealingly connected with a connector, the connector is also connected with a component such as a control handle. Additionally, the control system 10 is connected to a pedal switch. Delivery of pulses may be controlled by the control handle or the pedal switch. Alternatively, only the pedal switch may be provided. In this case, the component connected to the connector may be an extension cable. Either of these alternative control methods may be selected, as required.

A shock wave source 04 is provided on the inner tube 05. When a wall of the balloon 01 is pressed against a calcified lesion, the shock wave source 04 is activated to create pulses, which propagate through a conductive medium to a surface of a straight section of the balloon 01, where they strike the calcified lesion and crush calcific masses there, restoring elasticity of the blood vessel. The shock wave source 04 is electrically connected to the control system 10, and when the liquid is introduced into the balloon 01, the pressure sensors 02 monitor pressures within the balloon 01. When something abnormal occurs to the balloon 01 (e.g., leaking or rupturing), the pressure sensors 02 sense the resulting pressure change and feed data indicating the change back to the control system 10. The control system 10 can make a decision based on the pressure data. If the data indicates that a sudden pressure drop has taken place in the balloon, then it is determined that the system is operating abnormally, and the energy is cut off to prevent otherwise continued electric discharge from causing damage to a human body.

It is to be noted that the pressure sensors may be arranged in any suitable manner on the balloon, as required. For example, they may be arranged at intervals circumferentially, or axially, or both circumferentially and axially. FIG. 2 shows an example of the circumferential arrangement.

As shown in FIGS. 3 to 7, in this embodiment, the shock wave source 04 is composed of a number of sets of electrodes, each including a first electrode 0411, a second electrode 0412 and an insulator layer 0413. It is to be noted that the sets of electrodes may be in any suitable form, as required. Three example forms according to this embodiment are set forth below for the purpose of better illustration without being intended to be limiting in any sense.

Figure 3:
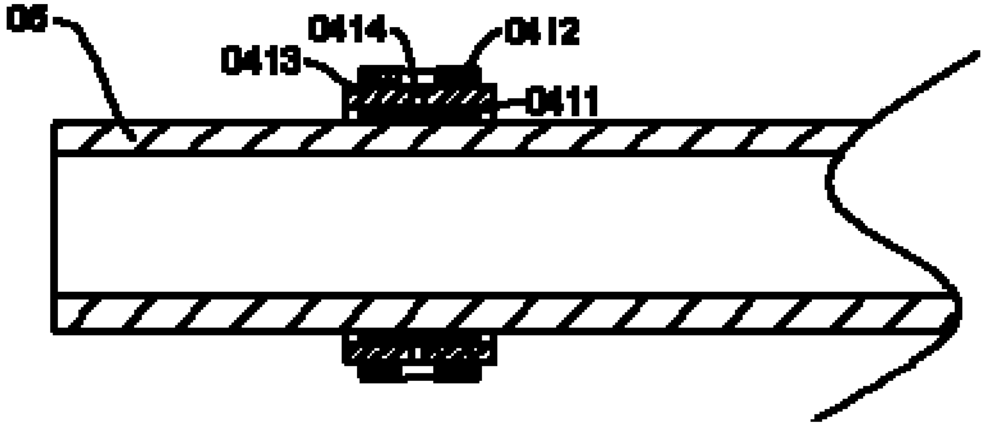
FIG. 3 depicts a schematic structural view of a first arrangement of sets of electrodes in a shock wave catheter according to an embodiment of the present application.
Figure 4:
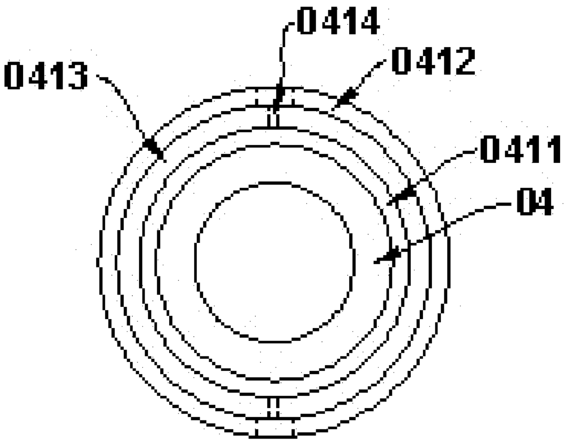
FIG. 4 depicts a cross-sectional view of the arrangement of electrodes sets of FIG. 3.

When the first electrode 0411 is embedded in the second electrode 0412, the insulator layer 0413 is present between the first electrode 0411 and the second electrode 0412. At least one (e.g., two) discharge aperture 0414 may be formed in each of the second electrode 0412 and the insulator layer 0413, as shown in FIG. 3.

Figure 6:
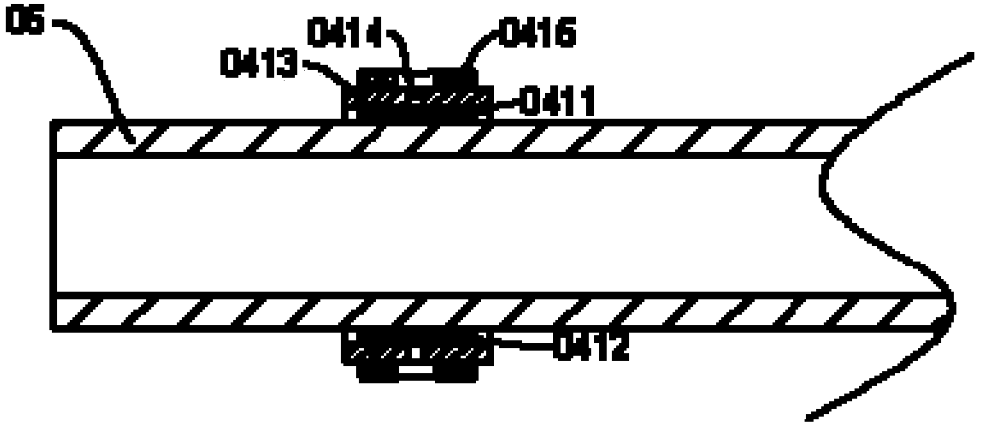
FIG. 6 depicts a schematic structural view of a third arrangement of sets of electrodes in a shock wave catheter according to an embodiment of the present application.

When both the first electrode 0411 and the second electrode 0412 are embedded in the insulator layer 0413, the first electrode 0411 and the second electrode 0412 are arranged on opposite sides of the inner tube 05. An outer electrode 0415 may be added to the exterior of the insulator layer 0413, and discharge apertures 0414 may be formed in the insulator layer 0413 and the outer electrode 0415, as shown in FIG. 6.

Figure 5:
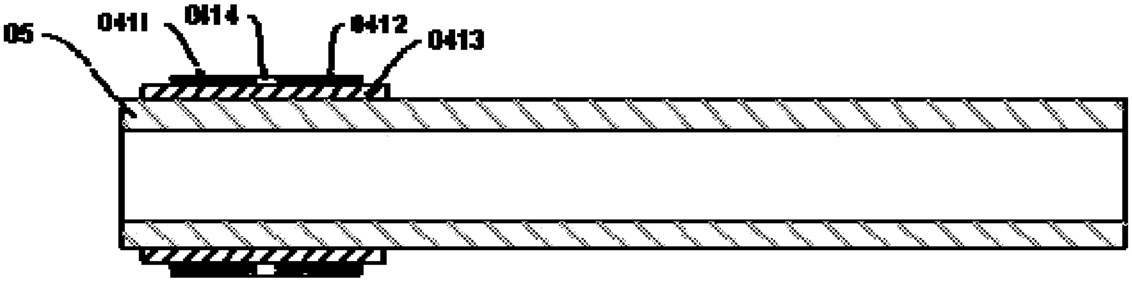
FIG. 5 depicts a schematic structural view of a second arrangement of sets of electrodes in a shock wave catheter according to an embodiment of the present application.

When the first electrode 0411 and the second electrode 0412 are juxtaposed, an insulator layers 0413 are respectively provided between the first electrode 0411 and the inner tube 05 and between the second electrode 0412 and the inner tube 05. A discharge aperture 0414 may be formed between the first electrode 0411 and the second electrode 0412, as shown in FIG. 5.

Figure 8:
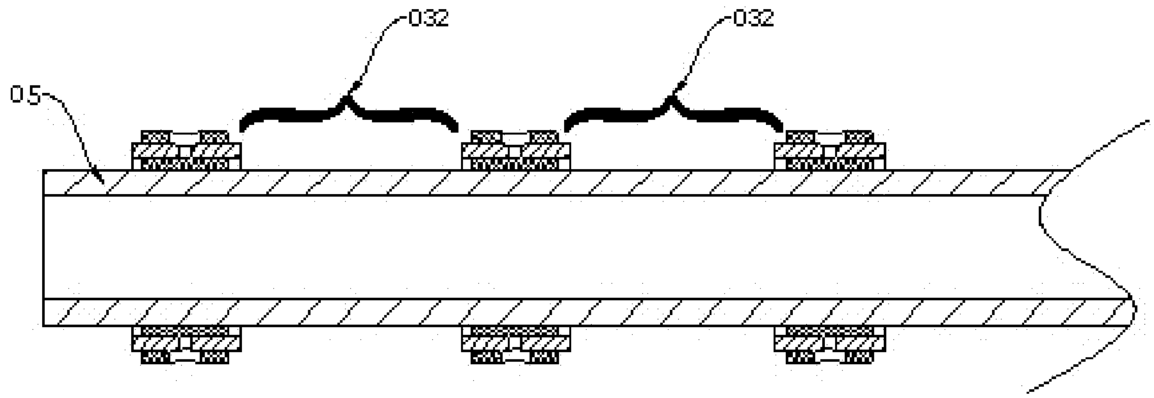
FIG. 8 schematically depicts an arrangement of a set of electrodes in a shock wave catheter according to an embodiment of the present application.
Figure 9:
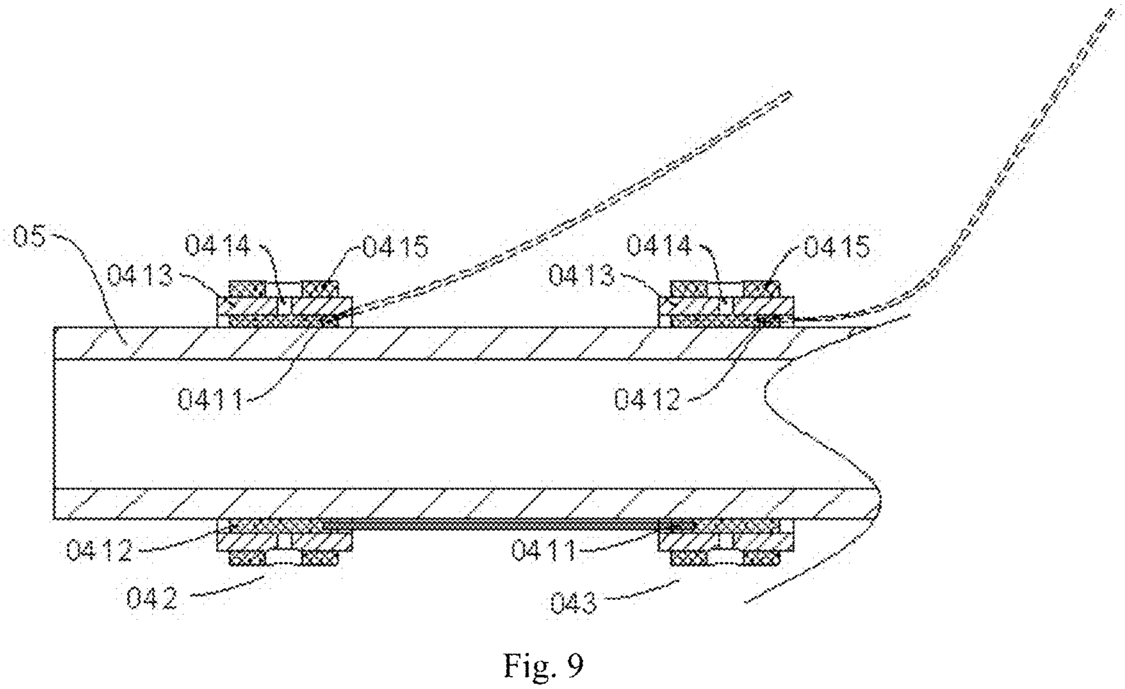
FIG. 9 depicts a schematic structural view of an arrangement of first and second sets of electrodes in a shock wave catheter according to an embodiment of the present application.
Figure 10:
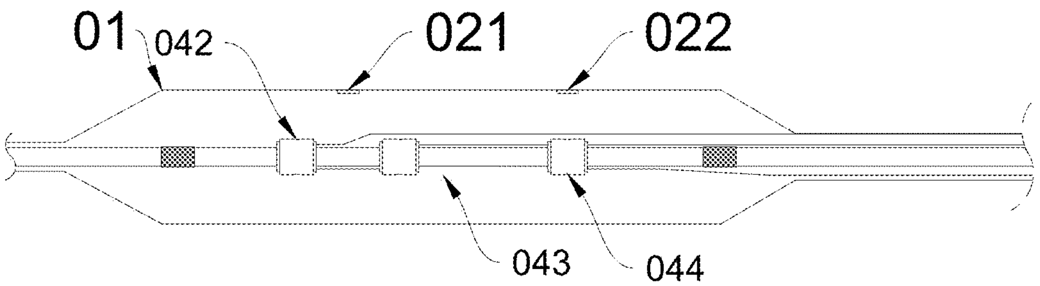
FIG. 10 depicts a schematic structural view of an arrangement of first, second and third sets of electrodes in a shock wave catheter according to an embodiment of the present application.

As shown in FIGS. 8 to 10, one embodiment of the present invention provides an electrode connection structure. When the shock wave source 04 is composed of one set of electrodes, a first electrode 0411 and a second electrode 0412 therein may be connected to the high-voltage generator by separate wires. When energy is applied to the shock wave source 04 from the high-voltage generator, arc discharge may occur between the first electrode 0411 and the second electrode 0412 in the shock wave source 04, creating shock waves which then travel through the balloon to a calcified lesion.

When the shock wave source 04 is composed of two sets of electrodes, each of first 042 and second 043 ones of the sets may include a first electrode 0411 and a second electrode 0412. Additionally, the first set of electrodes 042 and the second set of electrodes 043 may be connected to the high-voltage generator according to any of a number of connection methods. In a first connection method, the second electrode 0412 in the first set of electrodes 042 is wired to the second electrode 0412 in the second set of electrodes 043, and the first electrode 0411 in the first set of electrodes 042 and the first electrode 0411 in the second set of electrodes 043 are both wired to the high-voltage generator. In operation, a current may flow successively through the high-voltage generator, the first electrode 0411 in the second set of electrodes 043, the second electrode 0412 in the second set of electrodes 043, the second electrode 0412 in the first set of electrodes 042, the first electrode 0411 in the first set of electrodes 042 and again the high-voltage generator.

In a second connection method, the first electrode 0411 in the first set of electrodes 042 is wired to the first electrode 0411 in the second set of electrodes 043, and the second electrode 0412 in the first set of electrodes 042 is connected to the second electrode 0412 in the second set of electrodes 043 by another wire. The two connected pairs are then both connected to the high-voltage generator. In operation, a current may flow successively through the high-voltage generator, first electrode 0411 in the second set of electrodes 043, the first electrode 0411 in the first set of electrodes 042, the second electrode 0412 in the second set of electrodes 043, the second electrode 0412 in the first set of electrodes 042 and again the high-voltage generator.

When the shock wave source 04 is composed of two sets of electrodes, a first one 042 of the sets may include a first electrode 0411 and a second electrode 0412, and a second one 043 of the sets may include a first electrode 0411, a second electrode 0412 and an outer electrode 0415. In this case, the first set of electrodes 042 and the second set of electrodes 043 may be connected to the high-voltage generator according to any of a number of connection methods. In a first connection method, the second electrode 0412 in the first set of electrodes 042 is wired to the second electrode 0412 in the second set of electrodes 043, and the first electrode 0411 in the first set of electrodes 042 and the first electrode 0411 in the second set of electrodes 043 are wired to the high-voltage generator. In operation, a current may flow successively through the high-voltage generator, the first electrode 0411 in the second set of electrodes 043, the outer electrode 0415 in the second set of electrodes 043, the second electrode 0411 in the second set of electrodes 042, the second electrode 0412 in the first set of electrodes 042, the first electrode 0411 in the first set of electrodes 042 and again the high-voltage generator.

In a second connection method, the first electrode 0411 in the first set of electrodes 042 is wired to the first electrode 0411 in the second set of electrodes 043, and the second electrode 0412 in the first set of electrodes 042 is connected to the second electrode 0412 in the second set of electrodes 043 by another wire. The two connected pairs are then both connected to the high-voltage generator. In operation, a current may follow either a first path to flow successively through 1) the high-voltage generator, the first electrode 0411 in the second set of electrodes 043, the outer electrode 0415 in the second set of electrodes 043, the second electrode 0412 in the second set of electrodes 043 and again the high-voltage generator, or a second path to flow successively through 2) the high-voltage generator, the first electrode 0411 in the first set of electrodes 042, the second electrode 0412 in the first set of electrodes 042 and again the high-voltage generator. When the shock wave source 04 is composed of three sets of electrodes, each of the first set of electrodes 042, the second set of electrodes 043 and the third set of electrodes 044 may each include a first electrode 0411 and a second electrode 0412. In this case, the first set of electrodes 042, the second set of electrodes 043 and the third set of electrodes 044 may be connected to the high-voltage generator according to any of a number of connection methods.

In a first connection method, the first electrode 0411 in the first set of electrodes 042, the first electrode 0411 in the second set of electrodes 043 and the first electrode 0411 in the third set of electrodes 044 are connected in parallel, and the three parallel-connected electrodes are connected to the high-voltage generator. In addition, the second electrode 0412 in the first set of electrodes 042, the second electrode 0412 in the second set of electrodes 043 and the third electrode in the third set of electrodes 044 are connected in parallel, and all the three parallel-connected electrodes are connected to the high-voltage generator. In operation, a current may flow successively through the high-voltage generator, the first electrode 0411 in the third set of electrodes 044, the first electrode 0411 in the second set of electrodes 043, the first electrode 0411 in the first set of electrodes 042, the second electrode 0412 in the third set of electrodes 044, the second electrode 0412 in the second set of electrodes 043, the second electrode 0412 in the first set of electrodes 042 and again the high-voltage generator.

In a second connection method, the first electrode 0411 in the first set of electrodes 042 and the first electrode 0411 in the second set of electrodes 043 are wired in parallel to the high-voltage generator, forming a first channel. Moreover, the first electrode 0411 in the third set of electrodes 044 is wired to the high-voltage generator, forming a second channel. The second electrode 0412 in the first set of electrodes 042, the second electrode 0412 in the second set of electrodes 043 and the second electrode 0412 in the third set of electrodes 044 are connected to the high-voltage generator and serve as a return circuit. In operation, the first and second channels may be switched to enable repeated cycles of alternate simultaneous operation of the first set of electrodes 042 and the second set of electrodes 043 and operation of the third set of electrodes 044 alone.

In a third connection method, the first electrode 0411 in the first set of electrodes 042 is wired to the high-voltage generator, forming a first channel. The second electrode 0412 in the first set of electrodes 042 is wired in series with the second electrode 0412 in the second set of electrodes 043, and the first electrode 0411 in the third set of electrodes 044 is wired to the high-voltage generator, forming a second channel. The first electrode 0411 in the second set of electrodes 043 and the second electrode 0412 in the third set of electrodes 044 are connected to the high-voltage generator and serve as a return circuit. In operation, the first and second channels may be switched to enable repeated cycles of alternate simultaneous operation of the first set of electrodes 042 and the second set of electrodes 043 and operation of the third set of electrodes 044 alone.

These sets of electrodes may be connected in various series-connected, parallel-connected and series/parallel-connected combinations. A parallel connection allows simultaneous electric discharge from multiple electrodes, effectively avoiding frequent switching which may shorten the service life of the switch used and hence of the high-voltage generator. Moreover, a parallel connection allows the shock wave source to deliver shock waves with less energy, enabling safer use.

It is to be noted that the sets of electrodes may be spaced apart at interval(s) 032 properly determined as required. Adjusting the interval(s) 032 of the sets of electrodes can tune the energy of pulses that are delivered from the shock wave source 04 and travel to the balloon surface into a more even energy distribution, which enables more stable treatment, as shown in FIG. 8.

As shown in FIG. 9, in one embodiment of the present invention, the shock wave source 04 includes at least two sets of electrodes. For example, the shock wave source 04 may include at least a first set of electrodes 042 and a second set of electrodes 043. Additionally, a first electrode 0411 in the first set of electrodes 042 and a second electrode 0412 in the second set of electrodes 043 may be electrically connected to the control system 10, and a second electrode 0412 in the first set of electrodes 042 may be connected to a first electrode 0411 in the second set of electrodes 043. In this case, at least one of the pressure sensors 02 may be arranged on the balloon 01 at a location aligned with the midpoint of an interval between the first set of electrodes 042 and the second set of electrodes 043 to detect a pressure in response to delivery of shock waves from the first set of electrodes 042 and the second set of electrodes 043.

As shown in FIG. 10, the shock wave source 04 may include at least a first set of electrodes 042, a second set of electrodes 043 and a third set of electrodes 044. The first set of electrodes 042 may be adjacent to the second set of electrodes 043, and a second electrode 0412 in the first set of electrodes 042 may be connected to a second electrode 0412 in the second set of electrodes 043. One of a first electrode 0411 in the first set of electrodes 042 and a first electrode 0411 in the second set of electrodes 043 may be connected to a first electrode 0411 in the third set of electrodes 044 and to the control system 10. The other of the first electrode 0411 in the first set of electrodes 042 and the first electrode 0411 in the second set of electrodes 043 may be connected to the control system 10, along with a second electrode 0412 in the third set of electrodes 044. In this case, the pressure sensors 02 may include at least a first pressure sensor 021 and a second pressure sensor 022. The first pressure sensor 021 may be arranged on the balloon 01 at a location aligned with the midpoint of an interval between the first set of electrodes 042 and the second set of electrodes 043, and the second pressure sensor 022 may be arranged on the balloon 01 at a location aligned with the third set of electrodes 044. The first pressure sensor 021 may be used to detect a pressure around the first set of electrodes 042 and the second set of electrodes 043, and the second pressure sensor 022 is used to detect a pressure around the third set of electrodes 044. That is, each single pressure sensor 02 may be responsible for detecting a number of electrodes in the first 042, second 043 and/or third 044 sets.

Figure 7:
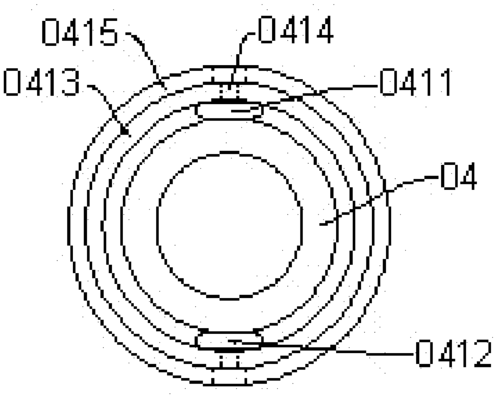
FIG. 7 depicts a cross-sectional view of the arrangement of electrodes sets of FIG. 6.

In operation of the shock wave source, the several sets of electrodes successively discharge electricity, and in the active time interval of each set, a corresponding pressure sensor 02 detects pressure information, which is then analyzed by the control system 10. When the detected pressure is much lower than a predetermined value, failure of the set can be determined. In this way, the failed set of electrodes can be located in a fast and accurate way. In one example as shown in FIG. 7, the shock wave source 04 is composed of a first set of electrodes 042, a second set of electrodes 043 and a third electrode 044, which are all connected to the control system 10. During operation of the shock wave source 04, the control system first energizes the first set of electrodes 042 and the second set of electrodes 043 to cause the first set of electrodes 042 and the second set of electrodes 043 to simultaneously deliver pulses. At the same time, a first pressure sensor 021 disposed on the balloon 01 between the first set of electrodes 042 and the second set of electrodes 043 starts operating to detect a pressure at the location where it is located on the surface of the balloon 01. After the first set of electrodes 042 and the second set of electrodes 043 have accomplished their intended task, the control system 10 cuts off the energy supply to the first set of electrodes 042 and the second set of electrodes 043 and then energizes the third set of electrodes 044 to cause it to deliver pulses. At this time, a second pressure sensor 022 disposed on the surface of the balloon 01 in positional correspondence with the third set of electrodes 044 starts operating to detect a pressure at the location on the surface of the balloon 01. Through controlling the shock wave source 04 to supply energy in this way, the control system 10 enables repeated cycles of alternate simultaneous operation of the first set of electrodes 042 and the second set of electrodes 043 and operation of the third set of electrodes 044 alone. Accordingly, the first and second pressure sensors 021, 022 operate alternately and cyclically for pressure detection. In the event of any set of electrodes failing to correctly deliver pulses, the corresponding one of the first and second pressure sensors 021, 022 will detect an abnormal pressure. Upon receiving the abnormal pressure, the control system may report an error and cut off power.

It is to be noted that the number of sets of electrodes, of which the shock wave source 04 is composed, may be determined as required. The two exemplary compositions of the shock wave source 04 shown in FIGS. 6 and 7 are presented merely to better illustrate the shock wave source 04 and are not intended to limit the shock wave source 04 to any particular structure. For example, the shock wave source 04 may be composed of a plurality of interconnected first and second sets of electrodes 042, 043, or of a plurality of interconnected first, second and third sets of electrodes 042, 043, 044.

Figure 11:
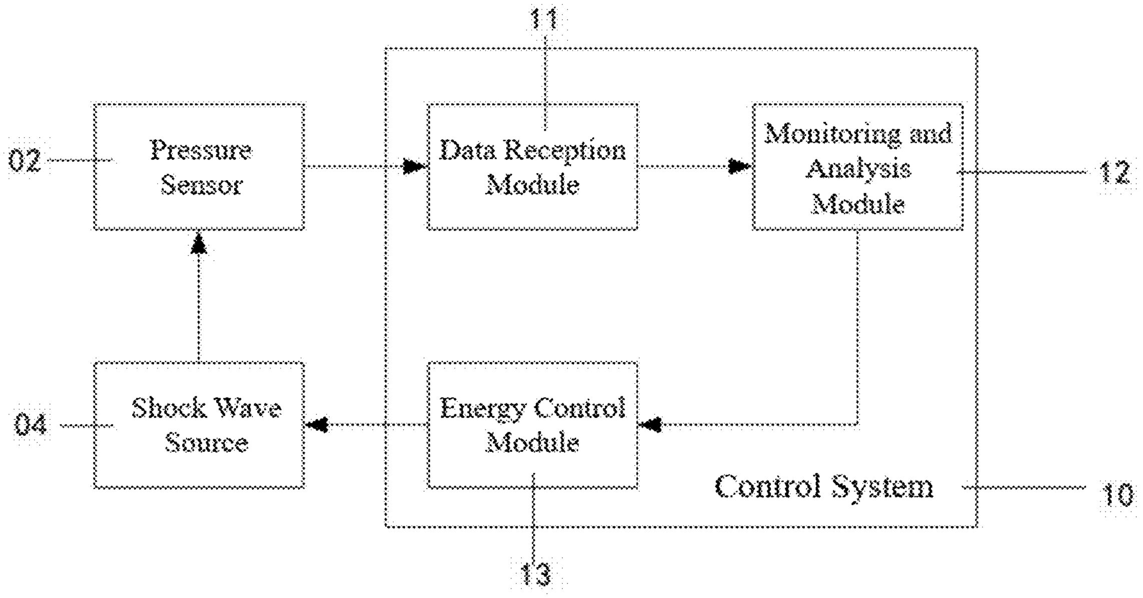
FIG. 11 depicts a schematic structural view of a control system according to an embodiment of the present application.

As shown in FIG. 11, one embodiment of the present invention provides a control system including:

- a data reception module 11 for receiving pressure values from pressure sensors 02 operating at different locations;
- a monitoring and analysis module 12 for analyzing a pressure profile indicated by the received values and thereby outputting a result of analysis; and
- an energy control module 13 for generating, based on the result of analysis, a control signal for adjusting energy with which a shock wave source 04 delivers pulses.

During operation of the shock wave source 04, the pressure sensors 02, which are arranged on a balloon 01, detect pressures on a surface of the balloon 01. The detected pressures are fed to the data reception module 11 and then analyzed in the monitoring and analysis module 12. A control signal is generated to the energy control module 13, based on a result of analysis. In the event of a rupture in the balloon 01, a pressure sensor 02 disposed around the rupture will detect the resulting pressure change. When the pressure change is founded in the monitoring and analysis module 12 to exceed a predetermined threshold, the energy control module 13 will generate a power-off signal for shutting down the shock wave source 04, avoiding possible damage caused to a human body by otherwise continued output of pulses.

When shock waves from the shock wave source 04 arrive at a pressure sensor 02, the pressure sensor 02 will detect a pressure at the time of arrival and feed the pressure to the data reception module 11 for analysis by the monitoring and analysis module 12. If the pressure lies within a predetermined range, then it indicates normal operation of a shock wave catheter. Otherwise, if the pressure is lower than a lower limit of the predetermined range, the monitoring and analysis module 12 will produce an adjustment signal and feed it to the energy control module 13. In response, the energy control module 13 will cause shock waves to be delivered with greater energy. As a result, a pressure detected by the pressure sensor 02 at the time of arrival of further shock waves from the shock wave source 04 will be within the predetermined normal range. Likewise, if the pressure is higher than an upper limit of the predetermined range, the energy control module 13 will automatically cause shock waves to be delivered with less energy. In this way, higher safety can be obtained in treatment using the system. A conductive medium may be introduced into the balloon 01, which may exhibit slight changes between different electrode conditions. Such changes may bring about attenuation of output energy from the shock wave source from the nominal value. The cooperation of the control system 10 with the pressure sensors 02 in terms of data feedback allows the energy control module 13 to automatically adjust the output energy to create an even shock wave energy distribution across a circumference along which the pressure sensors 02 are located, which enables more effective treatment of a lesion.

Treatment of a calcified lesion can be effected by shock waves from the shock wave source 04, which crush calcific masses within the lesion. In response to each delivery of a burst of shock waves from the shock wave source 04, the pressure sensors 02 on the surface of the balloon 01 will obtain a series of pressure values. For example, pressure values $P_{11}$, $P_{21}$, $P_{31}$ . . . may be collected from the pressure sensors 02 in response to the delivery of a first burst of shock waves from the shock wave source 04, $P_{12}$, $P_{22}$, $P_{32}$ . . . from a second burst of pulses, and $P_{1n}$, $P_{2n}$, $P_{3n}$ . . . from an n-th (where n is an integer ≥1) burst of pulses. The monitoring and analysis module 12 may analyze these pressure values by calculating pressure changes between pressure values obtained at a time interval spanning a certain number of shock wave bursts. For example, pressure changes between the pressure values resulting from the first and fifth burst of delivered shock waves may be calculated as $P_{15}-P_{11}$, $P_{25}-P_{21}$, $P_{35}-P_{31}$ . . . . From these pressure differences, it may be determined whether calcific masses at the locations of the pressure sensors 02 have been sufficiently crushed. Crushing of harder calcific masses in the lesion may require delivery of more bursts of shock waves. If pressure differences calculated after the delivery of a burst of shock waves remain lower than a certain range, it may be indicated that shock wave energy is not enough yet to crush calcific masses to a desired condition. In response, the monitoring and analysis module 12 may generate a signal to the energy control module 13, which instructs the latter to perform another cycle of operation. The energy control module 13 may adjust an output energy gradient (to allow more energy to be delivered to one or more locations where sufficient crushing has not been attained yet and allow the same or less energy to be applied to one or more locations where sufficient crushing has been achieved). This process may be repeated until all calcific masses have been satisfactorily crushed. This makes the system suitable for use in treatment of very heavily calcified lesions.

The principles of the present invention are as follows:

It includes a balloon 01 and a catheter body 07. The balloon 01 is connected to a distal end of the catheter body 07, the balloon 01 is provided thereon with a number of pressure sensors 02, the pressure sensors 02 are electrically wired to a control system 10. The catheter body 07 includes an outer tube 06 and an inner tube 05. The catheter body 07 defines a fluid passage through which a liquid can be introduced into or discharged from the balloon 01 to expand or contact the balloon 01 within a blood vessel. The liquid introduced or discharged through the fluid passage may be physiological saline or a contrast medium. The inner tube 05 is provided thereon with a shock wave source 04, which is activated, upon a wall of the balloon 01 starting pressing a calcified lesion, to deliver pulses capable of propagating the conductive medium to a surface of a straight section of the balloon 01, where they impinge on the calcified lesion to crush calcific masses therein to restore elasticity of the blood vessel. The shock wave source 04 and the pressure sensors 02 are each wired to the control system 10 so that, after the liquid is introduced into the balloon 01, the pressure sensors 02 can monitor pressures within the balloon 01, which represent a pressure profile. When the balloon 01 experiences an abnormal condition, the pressure sensors 02 sense an associated change in pressure and directly feed data indicating the change to the control system 10, which then make a determination based on the data. When an abnormality is determined, energy supply is cut off, avoiding possible damage caused to a human body by otherwise continued electric discharge.

Apparently, the embodiments described above represent only some, but not all, possible embodiments of the present invention. Any and all other embodiments derived from the embodiments disclosed herein by those of ordinary skill in this and related arts without paying creative effort are intended to fall within the scope of the invention. Any and all structures, devices and methods of operation that have not been described or explained in detail hereinabove may be implemented based on the common general knowledge in the art, unless otherwise specified or defined.

What is claimed is:

1. A shock wave catheter, comprising a balloon and a catheter body, wherein the balloon is connected to a distal end of the catheter body, the balloon provided thereon with at least one pressure sensor, the at least one pressure sensor configured for detecting pressures at different locations on a surface of the balloon, which represent a pressure profile, and the catheter body comprising an outer tube and an inner tube, the outer tube disposed over the inner tube, the catheter body defining a fluid passage configured for input and output of a medium into and from the balloon, the inner tube provided thereon with a shock wave source, the shock wave source configured for delivering pulses, wherein the at least one pressure sensor transmits the pressures that it detects on the surface of the balloon to a control system, the control system compares a change indicated by the pressures with a first predetermined threshold, if the change is greater than the first predetermined threshold, the control system deactivates the shock wave source and the shock wave source stops operating;

when the pressure values that the control system receives are higher than a first predetermined pressure value, the control system controls the shock wave source to deliver pulses with less energy;

when the pressure values are lower than a second predetermined pressure value, the control system controls the shock wave source to deliver pulses with more energy; when the pressure values are lower than a third predetermined pressure value, the control system generates an error report signal and stops output of pulses, the third predetermined pressure value is lower than the second predetermined pressure value;

in response to every delivery of shock waves from the shock wave source, the at least one pressure sensor collects a plurality of associated pressure values;

the control system analyzes the plurality of pressure values, calculates changes indicated by pressure values associated with pulses delivered at a time interval spanning a predetermined number of times of delivery, and if the changes indicated by the pressure values are lower than a lower limit of a range, the control system adjusts an energy input with gradient; and the shock wave source comprises a plurality of sets of electrodes, which are wired in parallel and connected to a high-voltage generator.

2. The shock wave catheter according to claim 1, wherein the at least one pressure sensor includes a plurality of the pressure sensors that are spaced apart on the balloon for pressure monitoring, the plurality of the pressure sensors are aligned with a set of electrodes of the sets of electrodes in the shock wave source.

3. The shock wave catheter according to claim 1, wherein each set of electrodes of the sets of electrodes in the shock wave source comprises a first electrode, a second electrode and an insulator layer, the first electrode embedded in the second electrode, the insulator layer situated between the second electrode and the first electrode, the second electrode and the insulator layer each defining a discharge aperture.

4. An electrode connection structure for use in the shock wave catheter according to claim 3, wherein the shock wave source comprises at least two or three sets of electrodes.

5. The electrode connection structure according to claim 4, wherein the shock wave source is composed of two sets of electrodes, the two sets of electrodes including a first set of electrodes and a second set of electrodes, the first set of electrodes and the second set of electrodes each comprise a first electrode and a second electrode, the first set of electrodes and the second set of electrodes are connected through the following connection manner:

the first electrode in the first set of electrodes is wired to the first electrode in the second set of electrodes, the second electrode in the first set of electrodes is wired to the second electrode in the second set of electrodes and that both pairs are connected to the high-voltage generator.

6. The electrode connection structure according to claim 4, wherein the shock wave source is composed of three sets of electrodes, the three sets of electrodes including a first set of electrodes, a second set of electrodes and a third set of electrodes, wherein the first set of electrodes, the second set of electrodes and the third set of electrodes each comprise a first electrode and a second electrode, the first set of electrodes, the second set of electrodes and the third set of electrodes are connected through the following connection manner:

connection manner i: the first electrode in the first set of electrodes, the first electrode in the second set of electrodes and the first electrode in the third set of electrodes are connected in parallel and then to the high-voltage generator and the second electrode in the first set of electrodes, the second electrode in the second set of electrodes and the second electrode in the third set of electrodes are connected in parallel and then to the high-voltage generator, or connection manner ii: the first electrode in the first set of electrodes and the first electrode in the second set of electrodes are wired in parallel and then to the high-voltage generator, forming a first channel, the first electrode in the third set of electrodes is wired to the high-voltage generator, forming a second channel, the second electrode in the first set of electrodes, the second electrode in the second set of electrodes and the second electrode in the third set of electrodes are connected to the high-voltage generator and switching is able to be made from each of the first and second channels to the other for electric discharge.

7. The shock wave catheter according to claim 1, wherein each set of electrodes of the sets of electrodes in the shock wave source comprises a first electrode, a second electrode and an insulator layer, the first electrode and the second electrode arranged side by side, the insulator layer situated between the first electrode and the inner tube and between the second electrode and the inner tube, the first electrode and the second electrode defining a discharge aperture therebetween.

8. The shock wave catheter according to claim 1, wherein each set of electrodes of the sets of electrodes in the shock wave source comprises a first electrode, a second electrode and an insulator layer, the first electrode and the second electrode both embedded in the insulator layer, the first electrode and the second electrode on opposite sides of the inner tube, the insulator layer surrounded by an outer electrode disposed on an exterior of the insulator layer, the insulator layer and the outer electrode each defining a discharge aperture.

9. The shock wave catheter according to claim 1, wherein during crushing of calcific masses in a heavily calcified lesion, pressure values detected by the at least one pressure sensor vary within a range, wherein if changes indicated by the pressure values are lower than a lower limit of a range, it is determined that the calcific masses have not been crushed yet, and the control system adjusts an energy input with gradient.

10. The shock wave catheter according to claim 1, wherein the control system further comprises:

a data reception module for receiving the pressure values from the at least one pressure sensor operating at different locations;

a monitoring and analysis module for analyzing a pressure profile that the received pressure values represent and outputting a result of analysis; and an energy control module for generating a control signal based on the result of analysis, the control signal is used to adjust energy with which pulses are delivered from the shock wave source.

11. The shock wave catheter according to claim 10, wherein when a change indicated by the pressure values that the monitoring and analysis module receives exceeds the first predetermined threshold, the energy control module generates a power-off signal, the power-off signal is used to deactivate the shock wave source and stop its output of pulses.

12. The shock wave catheter according to claim 10, wherein when the pressure values that the monitoring and analysis module receives are higher than the first predetermined pressure value, the energy control module controls the shock wave source to deliver pulses with less energy.

13. The shock wave catheter according to claim 10, wherein when the pressure values that the monitoring and analysis module receives are lower than the second predetermined pressure value, the energy control module controls the shock wave source to deliver pulses with more energy.

14. The shock wave catheter according to claim 10, wherein when the pressure values that the monitoring and analysis module receives are lower than the third predetermined pressure value, the energy control module generates the error report signal and stops output of the pulses.

15. The shock wave catheter according to claim 10, wherein when a change indicated by the pressure values that the monitoring and analysis module receives is less than the second predetermined threshold, the energy control module controls the shock wave source to deliver pulses with more energy.

* * * * *